(12) United States Patent
Brecher

(10) Patent No.: US 6,584,412 B1
(45) Date of Patent: Jun. 24, 2003

(54) APPLYING INTERPRETATIONS OF CHEMICAL NAMES

(75) Inventor: Jonathan Brecher, Cambridge, MA (US)

(73) Assignee: CambridgeSoft Corporation, Cambridge, MA (US)

( * ) Notice: Subject to any disclaimer, the term of this patent is extended or adjusted under 35 U.S.C. 154(b) by 285 days.

(21) Appl. No.: 09/632,406

(22) Filed: Aug. 4, 2000

Related U.S. Application Data

(60) Provisional application No. 60/147,067, filed on Aug. 4, 1999.

(51) Int. Cl.⁷ .......................... G01N 31/00; G06F 19/00
(52) U.S. Cl. ....................................... 702/27
(58) Field of Search .............. 702/22, 26–28, 702/30–32; 703/12

(56) References Cited

U.S. PATENT DOCUMENTS

| | | | | |
|---|---|---|---|---|
| 4,747,059 A | * | 5/1988 | Hirayama et al. | 703/12 |
| 4,811,217 A | * | 3/1989 | Tokizane et al. | 707/3 |
| 5,345,516 A | * | 9/1994 | Boyer et al. | 382/113 |
| 5,577,239 A | * | 11/1996 | Moore et al. | 702/27 |
| 5,950,192 A | * | 9/1999 | Moore et al. | 702/27 |
| 6,061,636 A | * | 5/2000 | Horlbeck | 702/22 |

OTHER PUBLICATIONS

Registry (Dictionary Searching) STN Database Summary Sheet (Mar. 1997, Revised), Chemical Abstracts Service, pp. 1–10.*

CRC Handbook of Chemistry and Physics, Student Edition, 76ᵗʰ Edition, 1995–1996, Section 2, pp. 2–22 through 2–26.*

Barnard, J.M., "Substructure Searching Methods: Old and New," *J. Chem. Inf., Comput. Sci. 33: pp. 532–538* (1993).

* cited by examiner

*Primary Examiner*—Marc S. Hoff
*Assistant Examiner*—Manuel L. Barbee
(74) *Attorney, Agent, or Firm*—Hale and Dorr LLP

(57) ABSTRACT

An interpretation of a chemical name is used to identify information pertaining to a substance identified by the chemical name, even if the chemical name is unfamiliar. Initially, a chemical name is acquired that identifies a chemical substance. Chemical structural information is derived from the chemical name. Based on the chemical structural information, a database entry or other resource is identified pertaining to the chemical substance.

16 Claims, 5 Drawing Sheets

APPLYING INTERPRETATIONS OF CHEMICAL NAMES

This application claims the benefit of U.S. Provisional Application Serial No. 60/147,067 entitled "APPLYING INTERPRETATIONS OF CHEMICAL NOMENCLATURE", filed on Aug. 4, 1999, which is incorporated herein by reference.

BACKGROUND OF THE INVENTION

This application relates to applying interpretations of chemical names.

A single chemical substance may have many chemical names ("synonyms"). For example, "methylene chloride" is synonymous with "dichloromethane" and "dichloromethane".

Identifying synonyms for a chemical substance allows resources associated with one of the synonyms to be designated as belonging together with resources associated with another of the synonyms. For example, if it is known that the chemical substance known as methylene chloride has a particular reactive property, and "dichloromethane" is known to be a synonym of "methylene chloride", the reactive property is understood to be associated with the name "dichloromethane" as well as the name "methylene chloride".

When a database of chemical information is searched by chemical name for a chemical substance, information in the database about the chemical substance may be missed by the search if the information is associated only with a synonym of the chemical name. The incidence of such misses may be reduced by associating, in the database, chemical substances with respective sets of known synonyms. In such cases, a search under a chemical name has a better chance of turning up the same information that would result from a search under a synonym. However, since many chemical substances have a large number of chemically accurate synonyms, including typographical variations and variations arising from differences in nomenclature conventions, it is often very difficult and impractical to include all such synonyms in the database. Accordingly, significant pertinent information in the database may still be missed by a search under a chemical name.

Searching by formula instead can lead to erroneous results, since different substances may have the same formula. For example, "$C_{13}H_{10}O$" is the formula for both benzophenone and 9-hydroxyfluorene.

SUMMARY OF THE INVENTION

An interpretation of a chemical name is used to identify a resource (e.g., information) pertaining to a substance identified by the chemical name, even if the chemical name is unfamiliar. Initially, a chemical name is acquired that identifies a chemical substance. Chemical structural information is derived from the chemical name. Based on the chemical structural information, a database entry or other resource is identified pertaining to the chemical substance. Thus, resources that are associated with a chemical substance can be identified highly reliably and with high accuracy, even in cases where the substance has many synonyms. In particular, information about the chemical substance can be found in a database even in cases where the database is searched under a chemical name that is not explicitly stored in the database. A database that is not filled with extensive lists of synonyms can yield search results comparable to results from a database that is replete with synonyms.

Other features and advantages will become apparent from the following description, including the drawings, and from the claims.

DETAILED DESCRIPTION

Figure 1:
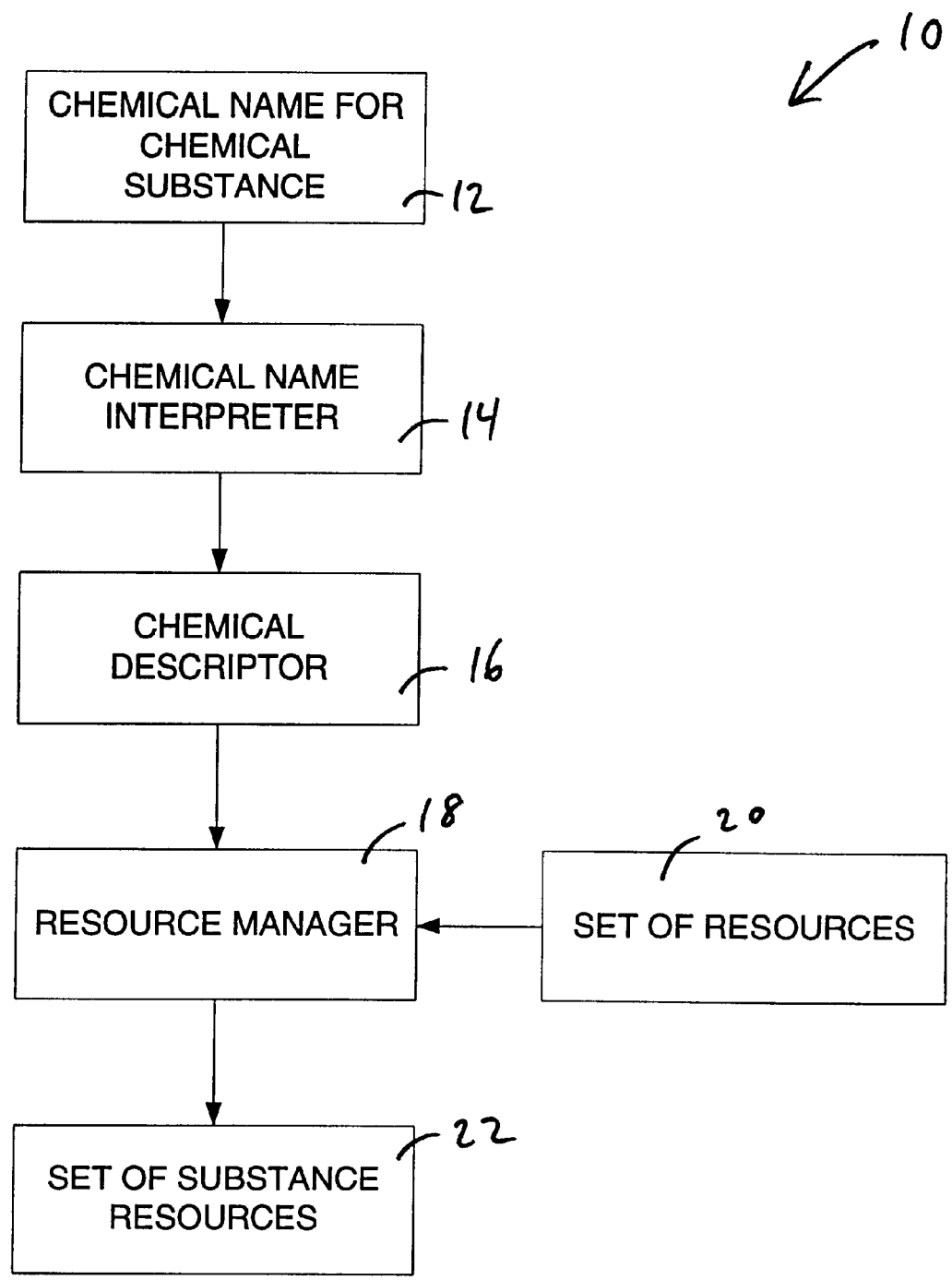
FIGS. 1–3 are block diagrams of computer-based systems.

FIG. 1 illustrates a system 10 in which a chemical name 12 is interpreted by a chemical name interpreter 14 to produce a chemical descriptor 16. Descriptor 16 is used by a resource manager 18 to determine, from a set of resources 20, a set of substance resources 22 that pertain to the chemical substance identified by the chemical name. The chemical name may include phonetic text such as "methylene chloride" and may include formulaic text such as "$CH_2Cl_2$".

Figure 2:
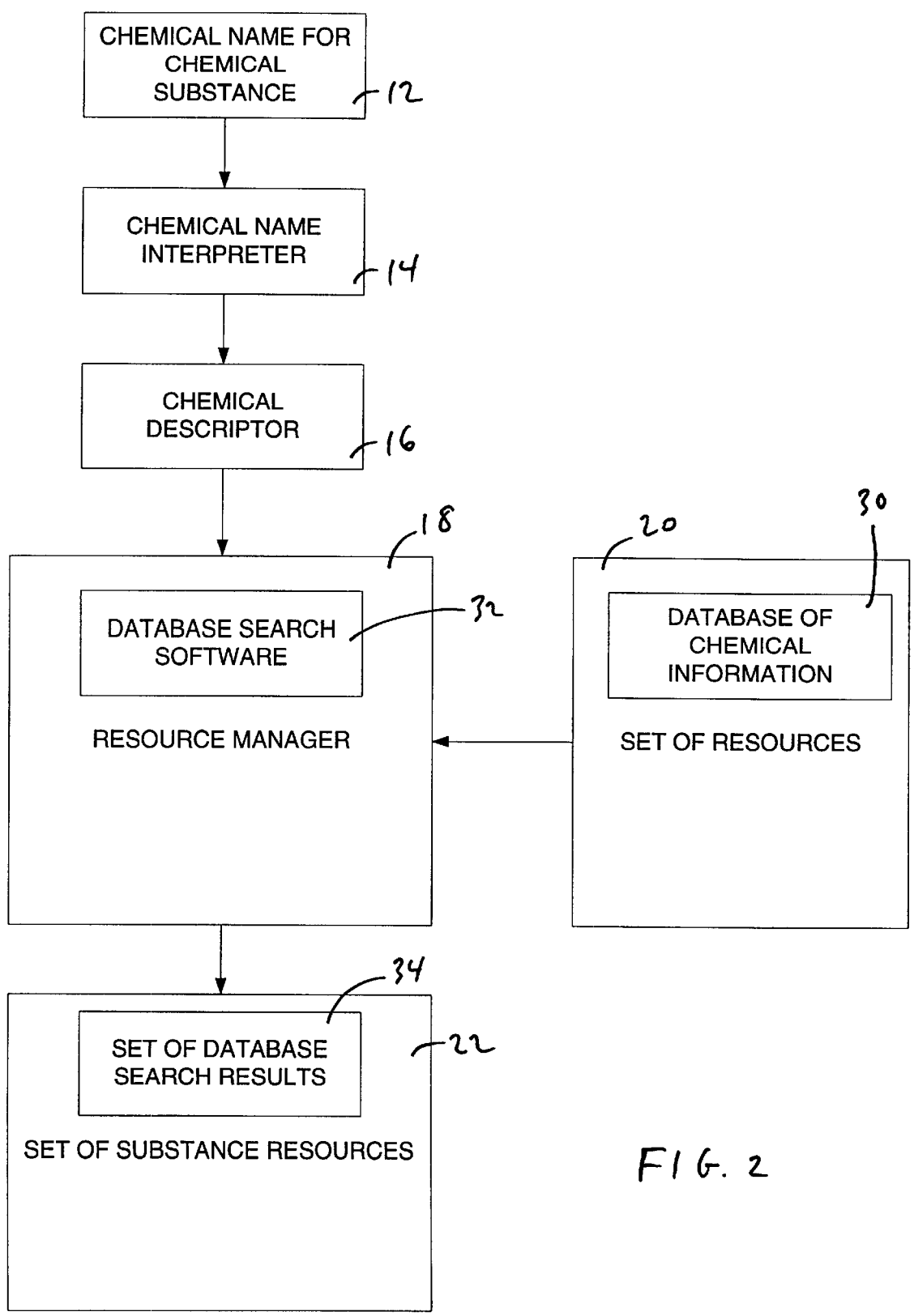

FIG. 2 illustrates a specific case in which the set of resources includes a database of chemical information 30, the resource manager includes database search software 32, and the set of substance resources includes a set of database search results 34. In a search of the database, the database search software applies the chemical descriptor to the database to produce the results 34 that include information from the database that pertains to the substance identified by the chemical name. Results 34 are produced even if the database does not include a reference to the particular chemical name that was interpreted. The database may include information concerning the chemical structure and physical properties of chemical substances.

Figure 3:
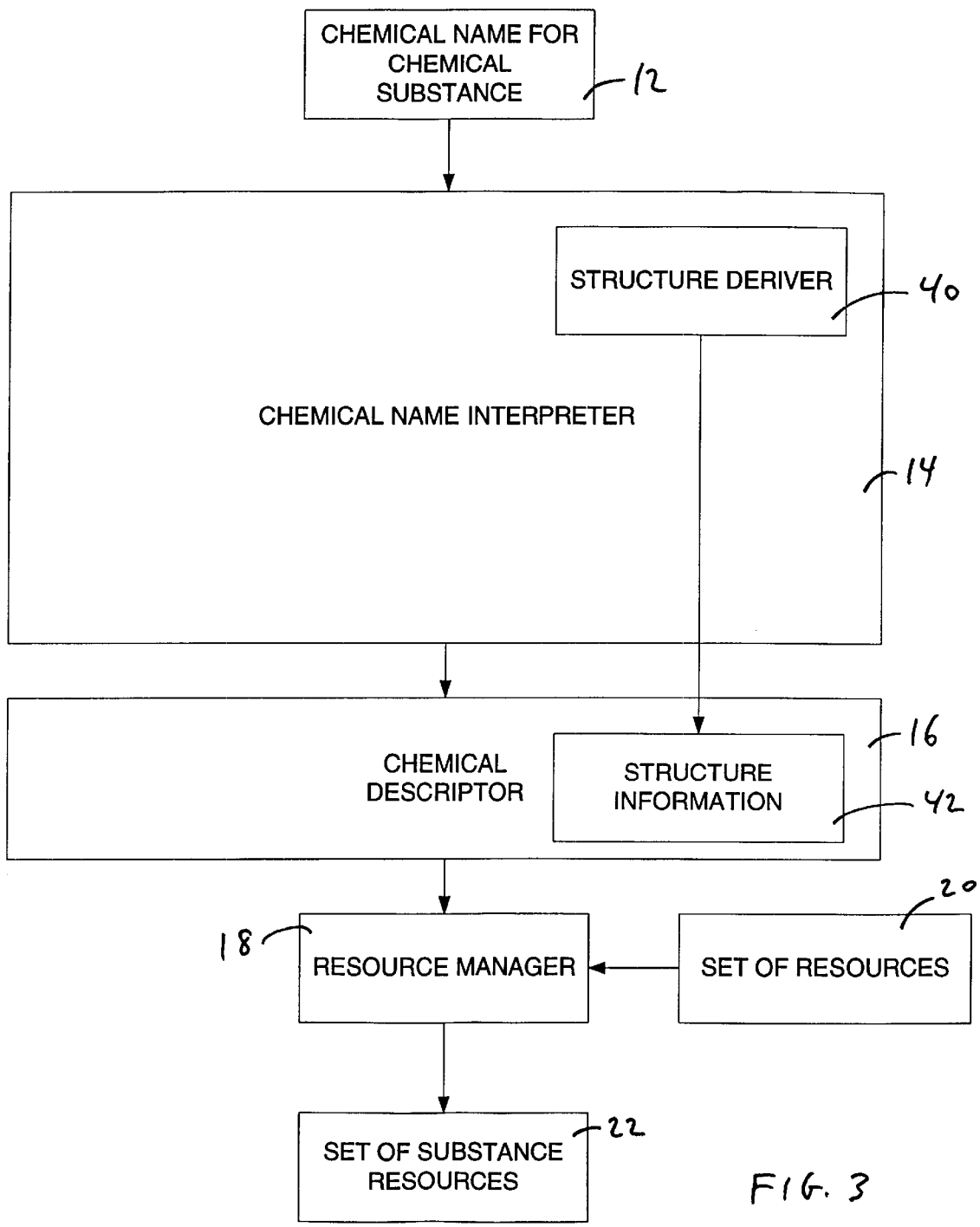

As shown in FIG. 3 and as described below, the chemical name interpreter may include a structure deriver 40 that derives information representing a chemical structure diagram 42 from the chemical name, and the chemical descriptor may include the structure diagram information. The database search software may use the structure diagram information in a structure-based search of the database. Thus, information in the database regarding a chemical substance can be found without searching directly under the chemical name.

Figure 4:
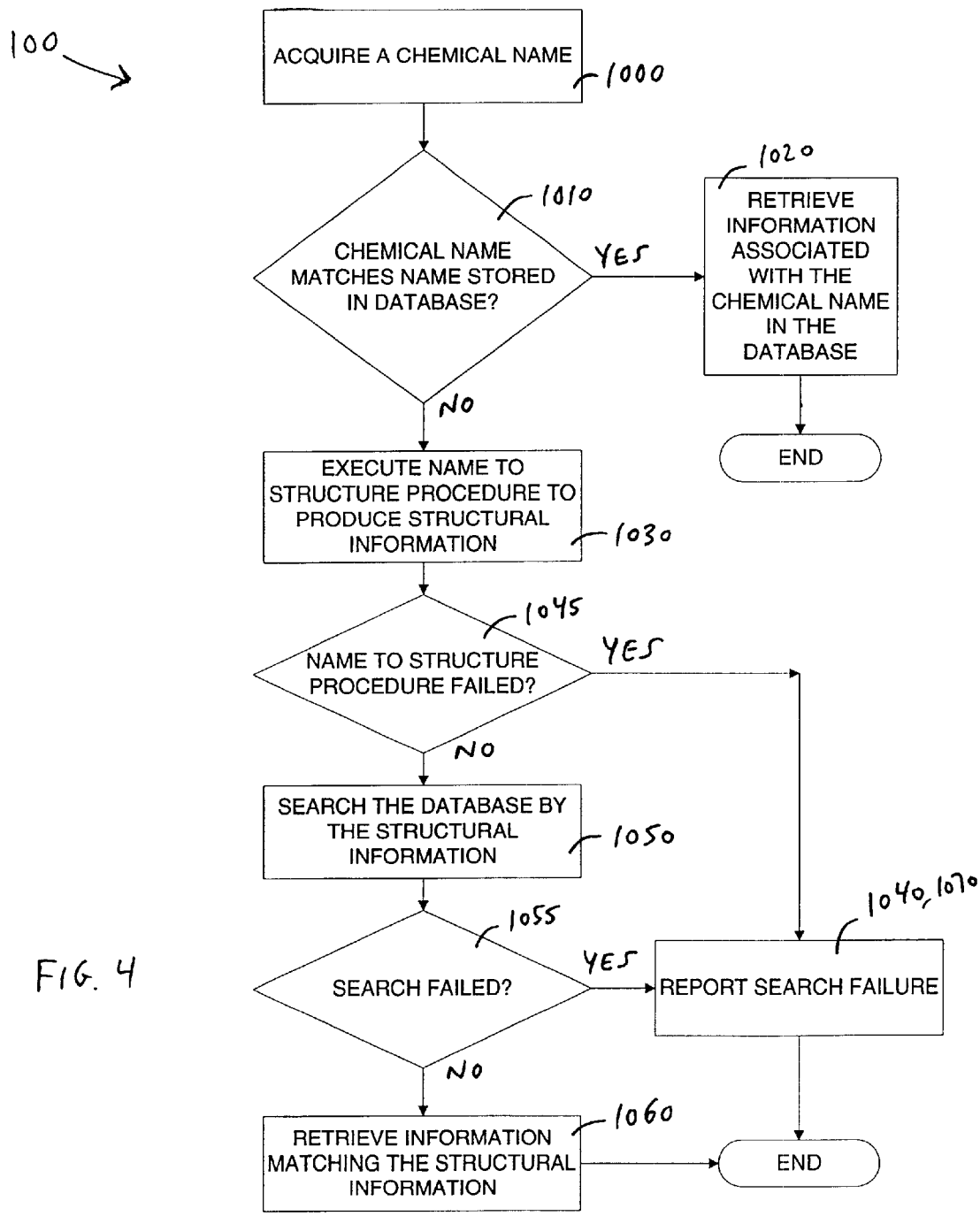
FIG. 4 is a flow diagram of a computer-based procedure.

FIG. 4 illustrates a procedure 100 for searching a database of chemical information. A chemical name is acquired (step 1000). For example, the chemical name may be supplied by a human user (such as by typing in the name at a keyboard) or by a computer program. In at least some cases, it is advantageous if it is determined whether the chemical name matches a chemical name stored in the database (step 1010). If a match is found, information associated with the chemical name in the database is retrieved (step 1020), and the procedure terminates.

If a match is not found, or if a name match is not attempted, a procedure for deriving structure diagram information from the chemical name ("name to structure procedure") is executed (step 1030). An example of the name to structure procedure is described in U.S. patent application Ser. No. 09/502,810, entitled "DERIVING CHEMICAL STRUCTURAL INFORMATION", filed Feb. 11, 2000, which is incorporated herein by reference. If the name to structure procedure fails, a search failure is reported (step 1040), and the procedure terminates.

If the name to structure procedure is successful (step 1045), the database is searched based on the structure diagram information (step 1050). Searching a database of chemical information by structure is well known in the art and is described, for example, in Barnard, J. M., "Substructure Searching Methods: Old and New", J. Chem. Inf. Comput. Sci. 1993, 33, 532–538.

If the database is found to contain one or more entries that match the structure diagram information (step 1055), information associated with the entries in the database is retrieved (step 1060), and the procedure terminates. If no such entry is found, a search failure is reported (step 1070), and the procedure terminates. In at least some cases, it is advantageous if, in a case in which the database includes one or more entries that match the structure diagram information, the acquired chemical name is added to the database before the procedure terminates.

Figure 5:
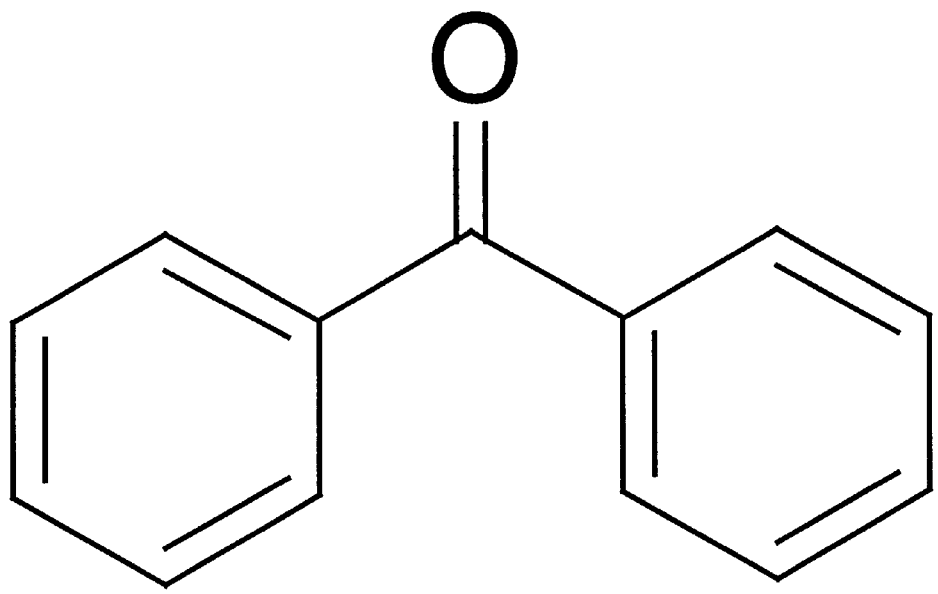
FIG. 5 is a diagram of chemical structural information.

For example, a chemist desiring to find information about "diphenylketone" would initiate a search of the database for database entries identified with the name "diphenylketone". If no match is found, structural information (depicted in FIG. 5) is derived from the name "diphenylketone". The structural information is used as the basis of a structural search of the database. Such a structural search might find a database record having information about a substance named "benzophenone". If so, the information about benzophenone is retrieved from the database and presented to the chemist. This result is appropriate, because "benzophenone" is a synonym for "diphenylketone" and the information about benzophenone is information sought by the chemist in the search.

In a further example, a database may consist of the following entries:

| Name | Formula | Melting Pt | Structure |
|---|---|---|---|
| benzophenone | $C_{13}H_{10}O$ | 48.5 | [structure for benzophenone] |
| 9-hydroxy-fluorene | $C_{13}H_{10}O$ | 154 | [structure for 9-hydroxyfluorene] |

In such a case, if a chemical name search is relied upon to find the melting point of diphenyl ketone, the melting point information will not be found, because the name "diphenyl ketone" is not present in the database. However, if information representing the structure of diphenyl ketone is derived, the structural information can be matched to the database's structural information for benzophenone. Thus, a search of the database using the structure of diphenyl ketone reveals that the melting point of diphenyl ketone is 48.5.

Procedure 100 can be applied to derive structural information from names in databases representing catalogs produced by commercial chemical vendors, which allows the contents of the catalogs to be evaluated for accuracy. In a specific example, the name to structure procedure is applied to all chemical names and synonyms in several catalogs, and each instance of produced structural information is examined for accuracy. As a result, discrepancies may be revealed. The discrepancies may be due to previously unnoticed errors in the database. In particular, entries of poor quality are exposed. For example, due to problems such as human error, maleic anhydride may be represented in the database by many lexicographically distinct variants, including "maleic anhydride" and "Msleic Snhydride".

All or a portion of the procedures described above may be implemented in hardware or software, or a combination of both. In at least some cases, it is advantageous if the technique is implemented in computer programs executing on one or more programmable computers, such as a personal computer running or able to run an operating system such as UNIX, Linux, Microsoft Windows 95, 98, 2000, or NT, or MacOS, that each include a processor, a storage medium readable by the processor (including volatile and non-volatile memory and/or storage elements), at least one input device such as a keyboard, and at least one output device. Program code is applied to data entered using the input device to perform the technique described above and to generate output information. The output information is applied to one or more output devices such as a display screen of the computer.

In at least some cases, it is advantageous if each program is implemented in a high level procedural or object-oriented programming language such as Perl, C, C++, or Java to communicate with a computer system. However, the programs can be implemented in assembly or machine language, if desired. In any case, the language may be a compiled or interpreted language.

In at least some cases, it is advantageous if each such computer program is stored on a storage medium or device, such as ROM or optical or magnetic disc, that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other embodiments are within the scope of the following claims. For example, interpretations of chemical names may be used in connection with any of many different types of computer-based resources. Such interpretations may be submitted to spreadsheet software for manipulation and use with the contents of spreadsheet cells, and to word processing software for editing and use with the text and graphics of documents. World-Wide Web pages may be derived from the interpretations. A World-Wide Web search engine may make use of the interpretations to facilitate searching for chemical information on the World-Wide Web.

What is claimed is:

1. A method for use in applying interpretations of chemical names, comprising:

acquiring a chemical name identifying a chemical substance;

determining whether said chemical name matches a chemical name stored in a database of chemical information;

if a match corresponding to said chemical name is not found, deriving chemical structural information from the chemical name; and based on the chemical structural information, identifying a resource pertaining to the chemical substance.

2. The method of claim 1, further comprising:

designating the resource as relating to the chemical name.

3. The method of claim 1, wherein the resource comprises a database entry associated only with at least one synonym of the chemical name.

4. The method of claim 3, wherein the database entry lacks the chemical name.

5. The method of claim 1, wherein the resource comprises database information.

6. The method of claim 5, further comprising adding the chemical name to the database information.

7. The method of claim 1, wherein acquiring the chemical name comprises receiving the chemical name from a computer program.

8. The method of claim 1, wherein acquiring the chemical name comprises receiving the chemical name from a human user.

9. The method of claim 1, wherein the resource comprises information concerning a chemical characteristic of the chemical substance.

10. The method of claim 1, wherein the resource comprises a database entry having information concerning a chemical characteristic of the chemical substance.

11. A method for use in applying interpretations of chemical names, comprising:

determining whether a chemical name matches a chemical name stored in a database of chemical information;

if a match corresponding to said chemical name is not found, attempting to derive chemical structural information from the chemical name in said database; and based on the results of the attempt, evaluating the database.

12. The method of claim 11, further comprising:

basing the evaluation on a typographical characteristic of the database.

13. A system for use in applying interpretations of chemical names, comprising:

an acquiror acquiring a chemical name identifying a chemical substance;

a determinor determining whether said chemical name matches a chemical name stored in a database of chemical information;

a derivor deriving chemical structural information from the chemical name, if a match corresponding to said chemical name is not found; and an identifier identifying, based on the chemical structural information, a resource pertaining to the chemical substance.

14. Computer software, residing on a computer-readable storage medium, comprising a set of instructions for use in a computer system to help cause the computer system to apply interpretations of chemical names, the instructions causing the system to:

acquire a chemical name identifying a chemical substance;

determine whether said chemical name matches a chemical name stored in a database of chemical information;

if a match corresponding to said chemical name is not found, derive chemical structural information from the chemical name; and based on the chemical structural information, identify a resource pertaining to the chemical substance.

15. A system for use in applying interpretations of chemical names, comprising:

a determiner determining whether a chemical name matches a chemical name stored in a database of chemical information;

an attemptor attempting to derive chemical structural information from the chemical name in said database if a match corresponding to said chemical name is not found; and an evaluator evaluating, based on the results of the attempt, the database.

16. Computer software, residing on a computer-readable storage medium, comprising a set of instructions for use in a computer system to help cause the computer system to apply interpretations of chemical names, the instructions causing the system to:

determine whether a chemical name matches a chemical name stored in a database of chemical information;

if a match corresponding to said chemical name is not found, attempt to derive chemical structural information from the chemical name in said database; and based on the results of the attempt, evaluate the database.

* * * * *